(12) United States Patent
Biesbrouck et al.

(10) Patent No.: US 9,182,417 B2
(45) Date of Patent: Nov. 10, 2015

(54) DEVICE AND METHOD FOR SEPARATING AND ANALYZING BLOOD

(75) Inventors: Gerardus Majella Biesbrouck, Santpoort Zuid (NL); Johannes Fredericus Carolus Glatz, Maastricht (NL)

(73) Assignee: FABPULOUS B.V., Maastricht (NL)

( * ) Notice: Subject to any disclaimer, the term of this patent is extended or adjusted under 35 U.S.C. 154(b) by 1217 days.

(21) Appl. No.: 12/992,262

(22) PCT Filed: May 14, 2009

(86) PCT No.: PCT/NL2009/050260
§ 371 (c)(1),
(2), (4) Date: Feb. 14, 2011

(87) PCT Pub. No.: WO2009/139632
PCT Pub. Date: Nov. 19, 2009

(65) Prior Publication Data
US 2011/0165589 A1   Jul. 7, 2011

Related U.S. Application Data

(60) Provisional application No. 61/127,688, filed on May 14, 2008.

(30) Foreign Application Priority Data

May 14, 2008 (NL) .................................. 2001577

(51) Int. Cl.
*G01N 33/53* (2006.01)
*G01N 33/92* (2006.01)
*G01N 33/543* (2006.01)

(52) U.S. Cl.
CPC .......... *G01N 33/92* (2013.01); *G01N 33/54366* (2013.01)

(58) Field of Classification Search
None
See application file for complete search history.

(56) References Cited

U.S. PATENT DOCUMENTS

| 3,481,477 | A |   | 12/1969 | Farr |
| 3,931,018 | A |   | 1/1976  | North, Jr. |
| 4,256,693 | A |   | 3/1981  | Kondo et al. |
| 4,458,020 | A | * | 7/1984  | Bohn et al. ................. 435/287.2 |
| 4,477,575 | A |   | 10/1984 | Vogel et al. |
| 4,918,025 | A | * | 4/1990  | Grenner ....................... 435/7.94 |
| 6,171,870 | B1 | * | 1/2001 | Freitag ........................... 436/518 |
| 6,506,167 | B1 | * | 1/2003 | Ishimito et al. ............... 600/577 |
| 6,632,681 | B1 |   | 10/2003 | Chu |
| 7,368,247 | B2 | * | 5/2008 | Hochstrasser et al. ......... 435/7.1 |
| 7,497,997 | B2 |   | 3/2009  | Glezer et al. |
| 7,745,228 | B2 |   | 6/2010  | Schwind et al. |
| 7,816,124 | B2 | * | 10/2010 | Samsoondar ............... 435/287.3 |
| 7,932,099 | B2 |   | 4/2011  | Egan et al. |
| 2002/0119147 | A1 | * | 8/2002 | Howell et al. ............... 424/140.1 |
| 2002/0160428 | A1 |   | 10/2002 | Sundrehagen |
| 2003/0175167 | A1 |   | 9/2003 | Takanori et al. |
| 2004/0014157 | A1 | * | 1/2004 | Sommer et al. ............... 435/7.93 |
| 2004/0133146 | A1 |   | 7/2004 | Broek et al. |
| 2005/0059921 | A1 | * | 3/2005 | Tu et al. ........................ 604/5.02 |
| 2005/0202513 | A1 |   | 9/2005 | Kitayama et al. |
| 2005/0274672 | A1 | * | 12/2005 | Tu et al. ......................... 210/645 |
| 2007/0031283 | A1 | * | 2/2007 | Davis et al. ..................... 422/58 |
| 2007/0092509 | A1 | * | 4/2007 | Mittra et al. ................ 424/140.1 |
| 2010/0311186 | A1 | * | 12/2010 | Gregory et al. ............... 436/501 |
| 2011/0009796 | A1 | * | 1/2011 | Tullis et al. .................. 604/5.02 |

FOREIGN PATENT DOCUMENTS

| CN | 1952664 | 4/2007 |
| DE | 29 22 958 | 12/1979 |
| EP | 0 508 010 | 10/1992 |
| EP | 1 152 241 | 11/2001 |
| EP | 1 346 773 | 9/2003 |
| GB | 2 392 854 | 3/2004 |
| JP | S54-178495 | 12/1979 |
| JP | S57-53661 | 3/1982 |
| JP | 2003-135435 | 5/2003 |
| JP | 2003-270239 | 9/2003 |
| JP | 2004-527760 | 9/2004 |
| RU | 2 358 267 | 6/2009 |
| WO | WO-02/40993 | 5/2002 |
| WO | WO-02/095409 | 11/2002 |
| WO | WO-03/083486 | 10/2003 |

OTHER PUBLICATIONS

International Search Report for PCT/NL2009/050260, mailed on Sep. 8, 2009, 4 pages.
International Preliminary Report on Patentability for PCT/NL2009/050260, issued Nov. 17, 2010, 8 pages.
International Search Report for PCT/NL2008/050072, mailed Apr. 7, 2008, 3 pages.
International Preliminary Report on Patentability and Written Opinion for PCT/NL2008/050072, Aug. 11, 2009, 7 pages.
Restriction Requirement in U.S. Appl. No. 12/526,394, dated Jun. 19, 2013, 6 pages.
Response to Restriction Requirement in U.S. Appl. No. 12/526,394, dated Jul. 31, 2013, 5 pages.
Non-Final Office Action in U.S. Appl. No. 12/526,394, dated Oct. 3, 2013, 16 pages.
Response to Non-Final Office Action in U.S. Appl. No. 12/526,394, dated Mar. 4, 2014, 10 pages.
Final Rejection in U.S. Appl. No. 12/526,394, dated May 8, 2014, 21 pages.
Response to Final Office Action and Request for Continued Examination in U.S. Appl. No. 12/526,394, dated Oct. 8, 2014, 14 pages.

* cited by examiner

*Primary Examiner* — Ann Lam
(74) *Attorney, Agent, or Firm* — Morrison & Foerster LLP

(57) ABSTRACT

The invention provides a device for detecting FABP in a blood sample from a patient, methods for analyzing blood on the presence of FABP, as well as methods and kits for the detection of FABP in a blood sample from a patient.

12 Claims, 4 Drawing Sheets

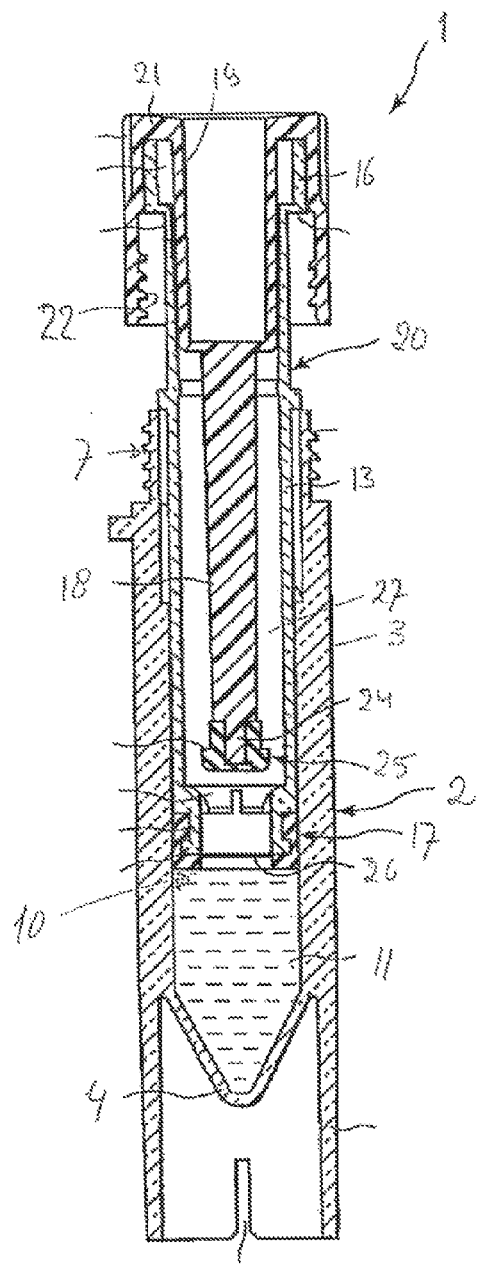
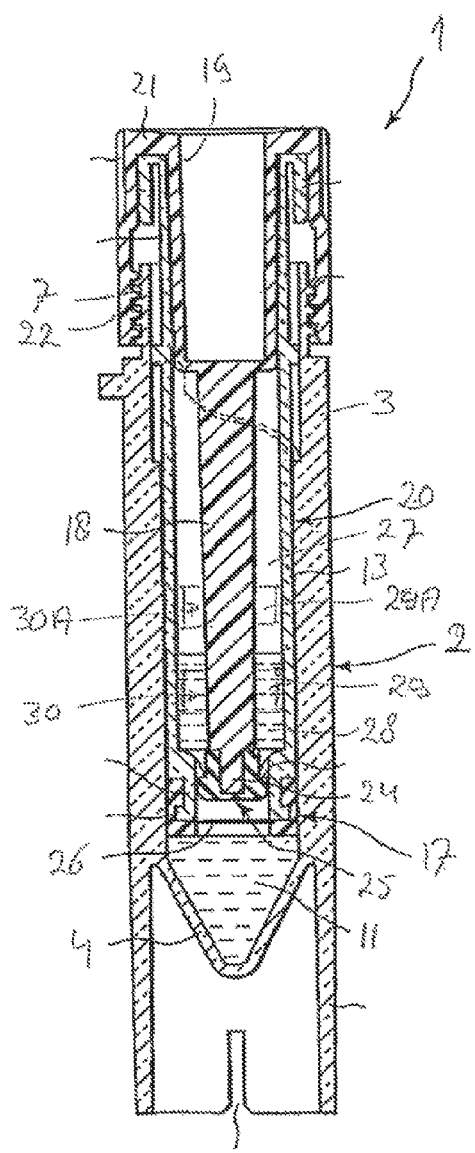
FIG.2
FIG.3

DEVICE AND METHOD FOR SEPARATING AND ANALYZING BLOOD

CROSS-REFERENCE TO RELATED APPLICATIONS

This application is the national phase of PCT application PCT/NL2009/050260 having an international filing date of 14 May 2009, which claims benefit of Netherlandic application No. 2001577, filed 14 May 2008, and which claims priority under 35 U.S.C. §119(e) to U.S. provisional application No. 61/127,688, filed 14 May 2008. The contents of the above patent applications are incorporated by reference herein in their entirety.

FIELD OF THE INVENTION

The invention relates to a device for separating blood and analyzing blood for the quantity of a protein present therein. In particular, the present invention relates to a device for analyzing fatty acid binding protein (FABP) in blood and a process for determining the amount of FABP in blood using the said device.

BACKGROUND OF THE INVENTION

Blood tests can be used to identify deviations from normal blood pictures, by virtue of which the presence of a pathological anomaly or a risk factor can, for example, be established, or it may at least indicate that further investigation is necessary or advisable. Of course, also a healthy blood picture can be established.

U.S. 2003/0175167 describes a device by which a quantity of blood can be taken up into a chamber, wherein the blood is diluted and then at least in part pressed through a filter. The filter is selected such that at least the blood plasma from the blood can pass the filter and be collected in a collection space, while at least the blood cells from the blood can not pass through the filter and remain in the chamber. Subsequently, a seal is provided in the passage between the chamber and said collection space, in order to prevent exchange of plasma and cells. The device is then send to a laboratory by mail, in order to carry out an analysis on the plasma. It is particularly important that the separation between the plasma and red blood cells is maintained, because otherwise the plasma is useless for many tests thereafter. The analysis of the blood plasma is done, for example, by spectral analysis.

U.S. 2004/0133146 describes a device, whereby blood is drawn using a thin tube, which blood is then delivered in a chamber, after which it is pressed against a filter with the help of a plunger, such that at least the blood plasma is forced through the filter and at least the red blood cells are left behind in the chamber. The separated blood plasma can then be examined, for example, by spectral analysis.

Compared to whole blood analysis, these devices provide the benefit that the blood does not need to be centrifuged. With this, it suffices to draw less blood and tests can be performed more quickly.

These prior art devices, and the methods in which they are used, have the disadvantage that they still require relatively long periods of time before a test result is known to the patient whose blood has been drawn or to the therapist. After all, while only small amounts of blood need to be drawn and while centrifugation is no longer required, the analysis must be carried out in a laboratory, so that relatively long periods of time are required for shipping and processing. Moreover, it may be experience as a disadvantage to the patient that others can become aware of the test results, even earlier than the patient himself.

Furthermore, a device is for example known from U.S. Pat. No. 4,477,575 wherein use is made of reagents, whereby a drop of blood is deposited on top of a filter. Driven by capillary action and/or gravity blood plasma is guided through a filter layer while the red blood cells are left behind on the filter. In or around the filtering layer a reagent is provided which can react with a substance in the blood plasma. Thereafter, a visual inspection of the visible surface of the device it can be established (through discoloration or emerging lines) whether or not the analyte is present in the blood. DE 29 22 958 describes multi-layer filters having different reagents for different pathological or otherwise indicative factors in blood.

Such a device offers the advantage that the test can be performed by a patient or in his or her presence, so that the time for obtaining the test results can be significantly shortened.

However such tests still require several tens of minutes or longer, which is undesirable in many cases. In addition, these tests have the disadvantage that they are very susceptible to, for example, contamination from outside, since the device is open, while in addition the degree of separation and thus the amount of blood plasma obtained cannot not be determined with sufficient precision. In particular when multi-layer filters are used with different reagents, this disadvantage is exacerbated because it is unclear how much blood plasma is provided to which layer of the filter and the runtime, and thus the time until result of the test, increases with the number of filter layers.

The invention aims to provide a device and/or process for analyzing blood for the presence of an analyte.

In particular, it is an objective of the present invention to provide a process and/or device for the relatively rapid separation of at least plasma and red blood cells from whole blood and then analyze at least the blood plasma. A further objective of the invention is to provide a process and/or device with which a user can perform a blood test autonomously and relatively fast.

It is another objective of the invention to provide a device and/or process for the separation and analysis of blood, which gives indications on thresholds or values of one or more analytes present in blood, in particular FABP.

SUMMARY OF THE INVENTION

In a first aspect, the present invention relates to a device for detecting FABP in a blood sample from a patient, the device comprising the following elements:
  a) separation means for separating blood plasma and red blood cells, wherein said separation means are provided with:
    a chamber for receiving of a blood sample and comprising a diluent for said blood sample;
    a filter through which blood plasma from a diluted blood sample and FABP, optionally complexed to an antibody, can pass but at least red blood cells not, and
    pressurizing means for pressing through said filter at least part of the blood sample for the provision of separated blood plasma, and
  b) collection means for collecting separated blood plasma, wherein said separation means and/or said collection means are provided with at least one of:

a detection-antibody against a first epitope of FABP, said detection-antibody being conjugated with a detectable label and capable of contacting separated blood plasma, and a capture-antibody against a second epitope of FABP which is different from said first epitope, wherein said capture-antibody is capable of being provided in said collection means in immobilized form and is capable of contacting separated blood plasma.

The term "capable of contacting" as used herein refers to the fact that the antibody is or can be in contact with the respective liquid (mostly the blood plasma) when the devise is used.

In a preferred embodiment where only a detection-antibody is provided, it is of advantage that the detection-antibody is able to complex with FABP in a detection reaction which takes place in liquid phase consisting essentially of diluted plasma containing homogeneously distributed detection-antibody, whereby the liquid phase is in direct contact with a detection surface present in said collection means and whereby the detection-antibody can be immobilized on said detection surface.

In a preferred embodiment of the device of the invention said filter is provided at or near the end of a tubular element which can be inserted in said chamber, wherein said collection means are formed by the interior part of said tubular element.

In another preferred embodiment said capture-antibody is immobilized at an insertion element which can be inserted into said collection means.

In still another preferred embodiment of the device of the invention said detection antibody is provided in said diluent.

In another preferred embodiment of the device of the invention said FABP is selected from the group consisting of H-FABP, L FABP, I-FABP, ILBP, B-FABP, A-FABP, E-FABP, T-FABP and M-FABP, and combinations thereof.

In another preferred embodiment of the device of the invention said detectable label is selected from the group consisting of colloidal gold or silver, streptavidin, biotin, microspheres, latex beads, peroxidase, streptavidin-labeled horse radish peroxidase (HRP), phosphatase, alkaline phosphatase (AP) chromogenic labels, fluorescent labels, phosphorescent labels, chemiluminescent labels and secondary antibodies, and a combination of these substances.

In yet another preferred embodiment of the device of the invention the collection means are at least partially transparent, so that (the site of attachment of) said immobilized capture-antibody is at least partially visible from the outside of said collection means or device.

The advantage of the device for the detection of FABP according to the present invention is that there is now provided a rapid test that gives test results within a few minutes. Typically, the test result is read within 3 minutes, preferably within 2 minutes, from the time of administration of a blood sample to the device. This important benefit is achieved by two important features of the device and the accompanying method. Firstly, in a preferred embodiment a detection reaction is used between a detection reagent and FABP which reaction takes place in a liquid phase consisting of diluted blood or plasma containing dissolved or suspended (homogeneously distributed) detection reagent, wherein said liquid is or is brought in direct contact with a detection surface. Such a detection reaction in liquid phase proceeds very quickly. Then diffusion of the reaction product of detection reagent and FABP takes place from the liquid phase to the detection surface. After immobilization at the detection surface the reaction product can be observed visually. This diffusion process is the rate limiting step in a preferred embodiment of the system for the detection of FABP according to the present invention, which system includes the application of the device as described herein. However, compared to the prior art systems, this is still very fast.

Secondly, use is made of a specific system to generate blood plasma. Where prior art systems use lateral flow principles to separate plasma from blood cells, the present system makes use of a filter with pressure means to achieve this. This also contributes greatly to the speed of the present system. That such a rapid test (about 10× faster than conventional) can be achieved in this way is unexpected in view of the fact that the system provides a first step in which the blood is diluted with a diluent before it is pressed through the filter. Nonetheless, the sensitivity of the test is sufficient to detect clinically relevant levels of FABP in the diluted blood plasma.

In another aspect, the present invention relates to a method for analyzing blood for the presence of FABP, wherein a (known) quantity of blood is separated into at least plasma and red blood cells, wherein at least the blood plasma is collected in collection means, wherein it is allowed that FABP present in the blood comes into contact with at least one antibody that specifically reacts with FABP, and wherein binding between the antibody and the FABP can be observed from the outside of that collection means.

In a preferred embodiment of a method of the invention a predetermined amount of blood is drawn from a subject or from a blood sample, and brought into the device, wherein it is mixed with a predetermined amount of diluent in order to obtain a desired dilution, whereafter the diluted blood is pressed against a filter, so that blood plasma is forced through the filter and into said collection means and red blood cells are held back by the filter.

In a preferred embodiment of the method of the invention the said plasma is contacted with said at least one antibody in said collection means.

In a further preferred embodiment of a method of the invention a detection-antibody is used against a first epitope of FABP, which detection-antibody is conjugated with a detectable label and which detection-antibody is provided in the device in such location that it can establish contact with separated plasma.

In a further preferred embodiment of the method of the invention a capture-antibody is used against a second epitope which is different from said first epitope of FABP, wherein said capture-antibody can be brought in immobilized state in said a collection means and is provided in the device in such location that it can establish contact with separated plasma.

In particular, there is provided a method wherein at least two antibodies are used each of which react specifically with a different epitope of FABP, namely a detection-antibody labeled with a detectable label and a capture-antibody for immobilization of the FABP-detection-antibody complex on a solid surface in the device, wherein both antibodies can bind simultaneously to FABP, wherein said detection-antibody is added to said diluent, and wherein said capture-antibody is immobilized at an insertion element or stem as herein defined and is brought into contact with separated plasma.

In another aspect, the present invention relates to a method for detecting FABP in a blood sample from a patient comprising the following steps:

providing a device of the present invention as described above;

introducing a known quantity of blood in said diluent in said chamber, whereby optionally a porous body is applied in which a fixed amount of blood can absorb in order to provide a predetermined amount of blood in the diluent, and mixing the blood with the diluent;

separating red blood cells from blood plasma by engaging the separation means of the device;

contacting FABP in said blood or blood plasma with at least one of said detection-antibody and capture-antibody under conditions wherein specific binding occurs between the antibody and the FABP, and detecting the specific binding.

Specific binding will for instance occur under conditions wherein one or both of FABP and the antibody are in a liquid, such as phosphate or other general buffer, under ambient temperatures and pressure. It is noted that the skilled person is well aware of the conditions wherein binding between an antibody and its antigen will occur.

In a preferred embodiment of a method of the invention said detection-antibody is provided in said diluent and it is ensured that said capture-antibody contacts the blood plasma in said collection means in immobilized state. This is preferably achieved by introducing into said plasma an element (for example, a stem or insertion element as herein defined) onto which said capture-antibody is immobilized. It is then allowed that the complex formed by FABP and the detection-antibody binds to the capture-antibody, wherein said element with immobilized capture-antibody adopts the function of detection surface.

In an alternative preferred embodiment of a method of the invention it is first allowed that a complex between FABP and detection-antibody is formed in a liquid (eg in diluted blood in the chamber or in diluted plasma in the collection means), which complex is then allowed to bind to said immobilized capture-antibody.

In another alternative preferred embodiment of a method of the invention only a detection-antibody is provided to a liquid selected from the diluent, the diluted blood and the separated plasma, and it is allowed that a detection-antibody-FABP complex is formed in that liquid or in a subsequent liquid which is formed by using the device, whereafter said complex is then allowed to immobilize (eg by applying paramagnetic beads to the detection reagent) to any surface of a space 27 (or first collection means 27) facing side of any element of the device 1 that limits space 27 so that the capture-antibody can be in direct contact with blood plasma 28. In fact, in such an embodiment the detection-antibody will also be capture-antibody.

In another alternative preferred embodiment of a method of the invention said FABP is selected from the group consisting of H-FABP, L FABP, I-FABP, ILBP, B-FABP, A-FABP, E-FABP, T-FABP, M-FABP and combinations thereof.

In another preferred embodiment of a method of the invention said detectable label is selected from the group consisting of colloidal gold or silver, streptavidin, biotin, microspheres, latex beads, peroxidase, streptavidin-labeled horse radish peroxidase (HRP), phosphatase, alkaline phosphatase (AP) chromogenic labels, fluorescent labels, phosphorescent labels, chemiluminescent labels and secondary antibodies, and combinations of these substances.

In a further aspect the present invention provides a kit-of-parts, comprising at least one device for separating blood in at least plasma and red blood cells wherein said device comprising a collection space for collecting the separated blood plasma, and at least one specific antibody that reacts with FABP suitable for being introduced into said collection space.

Preferably a kit-of-parts according to the present invention further comprises an element for taking up and releasing a predetermined amount of blood, such as for instance a sponge.

Preferably a kit-of-parts according to the present invention includes a device of the invention as described above.

Preferably the kit also comprises instructions for the performing a method of the invention, for operating said device and/or element, and/or for safely disposing of said used device and/or uptake element.

BRIEF DESCRIPTION OF THE DRAWINGS

For further illustration of the invention embodiments of a device and method in accordance with the invention will be explained on the basis of the drawings.

FIG. 2 shows a device of FIG. 1 in a partly engaged state wherein the tubular element is partially inserted into the chamber;

FIG. 3 shows a device of FIGS. 1 and 2 in a fully engaged state wherein the tubular element is fully inserted into the chamber;

In this description identical or corresponding elements have identical or corresponding reference numbers. Not all reference numbers are provided in all of the drawings. Reference number 57 in FIG. 4c does not correspond with reference number 57 in FIG. 5 as explained below.

DETAILED DESCRIPTION OF THE INVENTION

Figure 1:
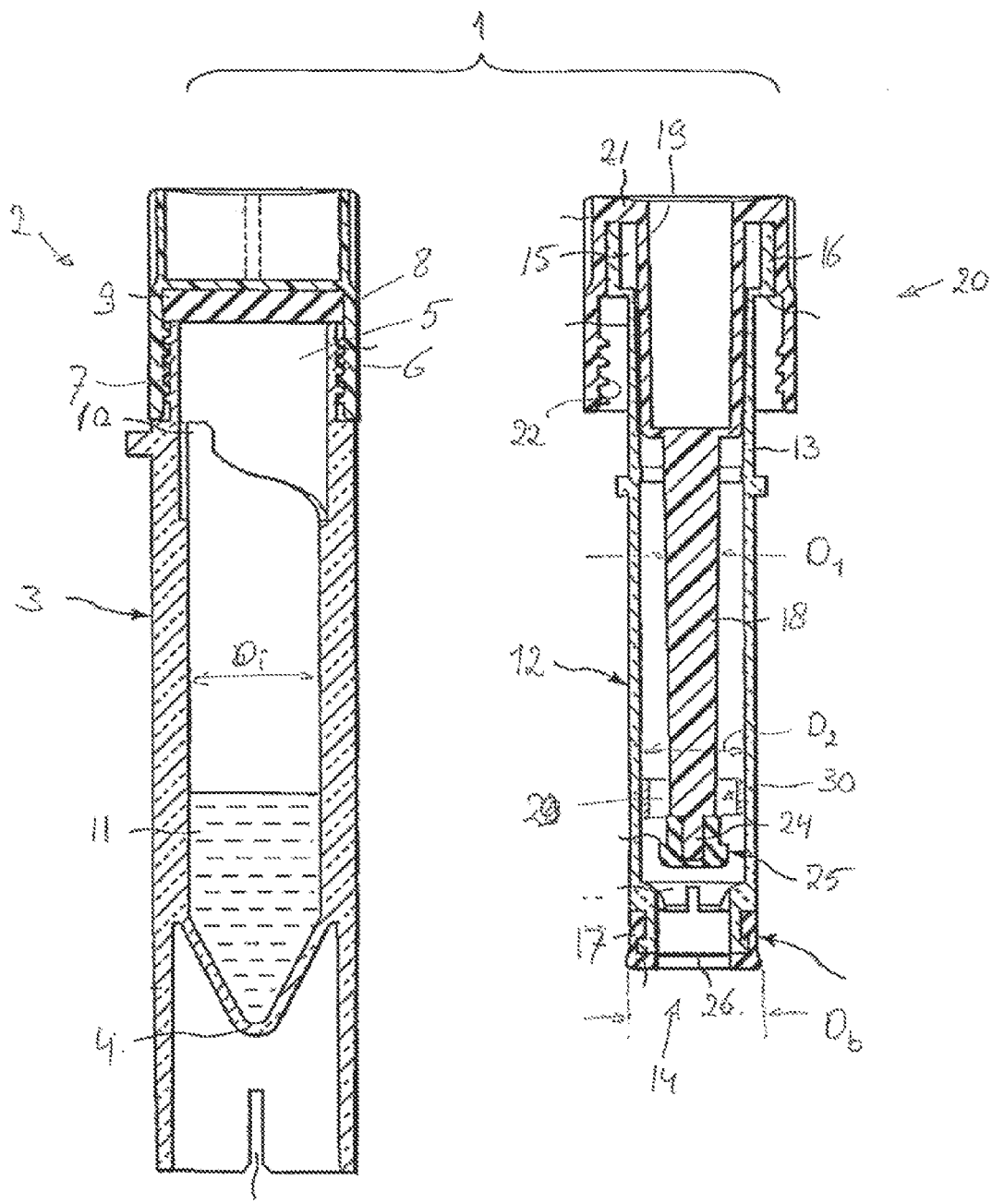
FIG. 1 shows a cross sectional view prior to use of a device of the invention, in a first embodiment.

In a first embodiment a device of the invention is characterized in that at least separation means for separating blood plasma and red blood cells are included, which separation means comprise pressure means for pressing at least part of the blood through a filter, wherein at least first collection means are provided for the collection of separated blood plasma and at least one reagent which is provided in said first collection means or which can be inserted therein to react with substances or organisms present in said blood plasma.

Such a device provides the advantage that at least blood plasma is separated from at least red blood cells under pressure, making the obtainment of the desired separation of blood plasma and red blood cells almost instantaneous. Furthermore, at least the blood plasma is collected in collection means in which the plasma is contacted or can be brought into contact with at least one reagent, so that it can be determined in a very short time (in minutes or seconds) whether a particular substance is present in the blood of a certain patient, or at least surpasses a certain value or limit. Preferably use is made of reagents that allow visual determination of whether or not a certain reaction takes place, for example by color chance, structural change such as coagulation, dissolution or the like.

The plasma is preferably collected in the first collection means, provided in the form of a space separated from the outside environment, so that no pollution, contamination or leakage of blood plasma can occur. Preferably, prior to use, the device is provided with a known quantity of diluent, in particular in the chamber, while in addition a known quantity of blood is provided in the chamber, so that the degree of dilution of the blood is accurately known. This ensures that rapid and accurate test results are easily obtained.

In a first particularly advantageous embodiment the at least one reagent is supplied or made available in the first collection means, especially at a wall part thereof. Preferably said wall part is at least partially transparent so that, for example, a change in color or texture of the reagent is clearly visible from the exterior of the device, at least from the exterior of first collection means, without the need of opening the device.

In an alternative embodiment the at least one reagent is provided on, in, or at an element which can be inserted into the first collection means. That provides at least the advantage that the device essentially can be implemented universally, wherein always a suitable reagent can be chosen, depending on the test to be performed.

The reagent in a device and/or method of the invention is preferably selected and/or dosed such that a transition value may be determined, so that at least it can be determined whether a particular factor in the blood is above or below a predetermined value.

In a special embodiment the device is equipped with a piston which can press the blood, or at least the blood plasma, through a filter, whereby the first collection means are preferably provided inside the piston. The at least one reagent can be provided on or in the piston.

In a device and method in accordance with the invention each time one reagent can be applied but also combinations of reagents can be provided for the simultaneous implementation of a series of tests in one device. For instance, on a wall part of the first collection means, rings or surfaces can be provided of different reagents. If need be, a reagent may of course also be provided in another aggregation condition, such as liquid or in the form of a solid.

In an alternative embodiment the at least one reagent is provided in or on a separate container, in which the device for separating the blood, particularly in the first collection means, is equipped with a pouring opening so that the blood plasma after its separation from the red blood cells, can be poured into or onto said container, at least said at least one reagent.

The at least one reagent is preferably selected from the group of reagents that merely indicate the presence of a substance or organism in the blood plasma and do not indicate a value for the concentration thereof. Preferably, the at least one reagent is essentially binary: reaction of the reagent indicates, for example by color, clotting or otherwise a transformation of the reagent, the blood plasma or a reaction between them, whether a certain threshold is exceeded or not.

The embodiments shown and discussed herein are always based on separation and analysis of blood. However, other biological samples can be tested with the same or a similar device. The embodiments of devices, methods and reagents given in the examples are shown for illustrative purposes only and do not limit the invention in any way.

In FIG. 1 a partial cross sectional view is provided of a device 1, according to the invention shown in a first embodiment in two parts. In FIG. 1 at the left side a first part 2 is shown, formed by a transparent plastic shell 3, which is closed at a bottom by a tapered bottom 4 and which is open on the opposite side 5. The open side 5 is equipped with neck 6 with an outer screw thread 7 onto which a cap 8 is screwed. The cap 8 clamps a gasket 9 at the neck 6, so that the interior room or chamber 10 within the shell 3 is closed. In the chamber 10 a diluent 11 is provided in a predetermined amount.

FIG. 1 shows at the right side second part 20 in the form of a piston part 12, comprising an at least partially transparent tubular element 13 having an open bottom 14 and an opposite open top 15, surrounded by a flange 16. Around the outside of the bottom 14 a flexible ring 17 is fitted having an outer diameter Db which fits in a manner described below with the inner diameter Di of shell 3 of first Part 2. In the tubular element 13 a stem 18 is introduced, which has an outer diameter d1, which is smaller than the inner diameter d2 of the tubular element 13. At the top of the stem 18 a flange part 19 is provided which at the top side connects to an apron 21 that extends outwards and is equipped with inner screw thread 22 that can fit onto the outer screw thread 7 of Part 2. The flange part fits sealingly in the top 15, while the apron can adjoin against the outside of flange 16. The stem 18 and flange part 19 are of such length that in the position displayed in FIG. 1 the lower end 24 of stem 18 remains at some distance from the lower end 14 within the tubular element 13. At the lower end 24 of the stem 18 a stop 25 is provided, which will be explained below. In the bottom end 14 of the tubular element 13 a filter 26 is affixed through which at least plasma can pass but through which red blood cells can not pass, at least by any dilution of the blood. Examples of using filters and dilutions are given in U.S. 2003/0175167 A1, which is incorporated by reference herein an which should not be interpreted restrictively.

In FIG. 2 the second part 20 is shown in a state wherein it is partially introduced or engaged into the first part 2, wherein a drop of blood of known volume is mixed in the diluent. In this position, the filter 26 sits on the diluted blood and seals the ring 17 against the inside of the shell 3. Thereby the chamber 10 is closed. From this position, the second section 20 can be pushed further downward in the direction of the bottom 4. The filter 26 will thereby press with force against the diluted blood, so that blood plasma is pressed upward through the filter 26 while the red blood cells are held back and remain in the chamber 10. Between the stem 18, the tubular element 13, the filter 26, and the flange part 19, first collection means 27 are formed in the form of an annular chamber, in which the blood plasma is collected.

In FIG. 3 a cross sectional side view of a device 1 according to the invention is shown, with the second part 20 pressed fully downward into the first part 2 to such an extend that the inner screw thread 22 is screwed on the outer screw thread 7 and the stop 25 seals the open-ended part of the tubular element 13 above filter 26, so that reverse flow of blood plasma 28 from the first collection means 27 back into the chamber is prevented.

In the embodiments shown in FIGS. 1 to 3 at least one surface 29 is provided on the inside of the tubular element 13 which contains a reagent 30 for at least one component or analyte present, or potentially present, in the blood plasma 28. Preferably, the reagent 30 is applied as an annular plane, so that it is visible from all sides from the outside of the composite device 1. This allows clear observation of the reaction of the reagent 30 with said analyte, for example by color change, structural change, coagulation, dissolution or the like, in case this analyte is present in the blood plasma to a certain extent. It will be clear that the reagent 30 or reagents can be chosen on the basis of the analytes whose presence, concentration, level or the like must be established. If desired, two or more surfaces 29, 29A, 29B, 29C . . . are provided with the same reagent 30 but preferably with different reagents 30A, 30B, 30C . . . .

Figure 6:
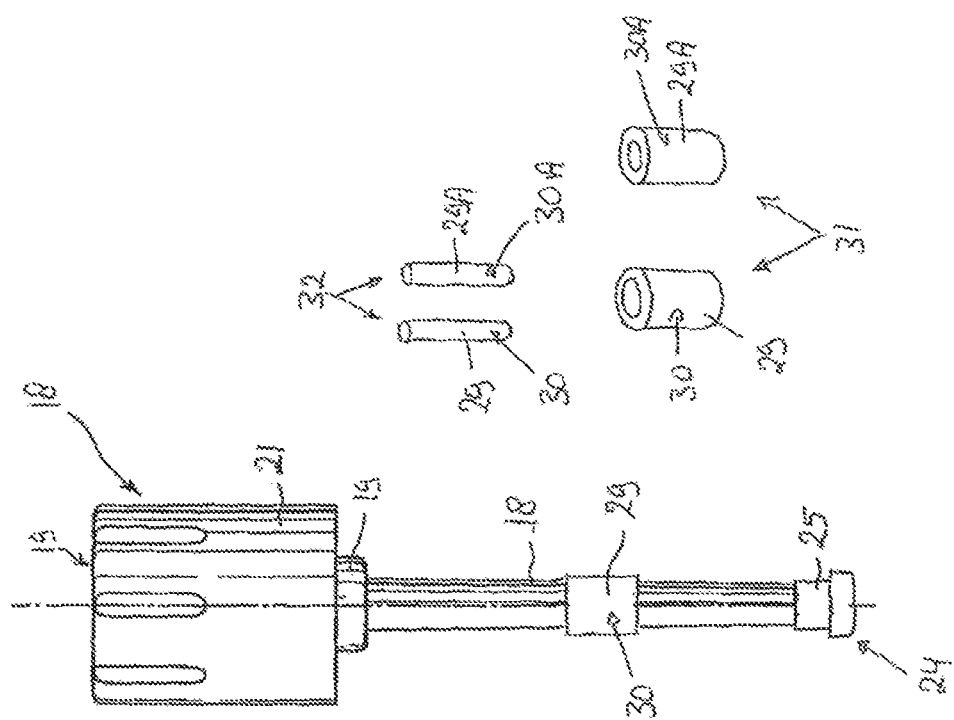
FIG. 6 shows an insertion element of a device of FIG. 1, in an alternative embodiment.

In an alternative embodiment shown in FIG. 6 the reagent is provided on stem 18 in the form of an annular surface 29. This has as an advantage that stem 18 can be chosen from, for example, a set of stems 18 with different reagents, depending on the desired analytes to be determined. Actually, this can of course also be achieved with various tubular elements 13 having different reagents.

In an alternative embodiment of a device of the invention a series of insertion elements such as (hollow) rods 31, rings 32 or the like can be provided as shown schematically in FIG. 6, wherein the various insertion elements carry different reagents 30, 30A, 30B . . . . This facilitates that at any time, depending on the desired test, a suitable reagent or a suitable combination of reagents can be provided in the tubular element 13. Annular elements may, for instance, be slided over the stem 18 in order to form a stem 18 as shown in FIG. 6. Rods or the like may for instance be placed in slots or openings in the stem 18 or in a stem 18 surrounding sheet or chamber, such as space 27 or tube 13, for example loosely inserted.

Figure 5:
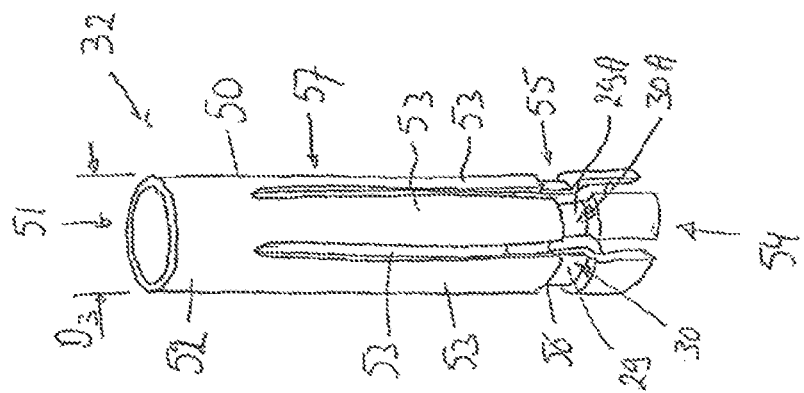
FIG. 5 shows schematically an insertion element for use in a device of the invention.

FIG. 5 shows a schematically perspective view of an alternative embodiment of a insertion element 32 for use in a device of FIGS. 1 to 3. This insertion element 32 is essentially formed by a hollow cylindrical body 50, that comprises at a first end 51 an annular section 52, from which a number of fingers 53 extend in the direction of an opposite second end 54. The fingers 53 have near the second end 54 a rejuvenation 55 because a section 56 of each finger is warped inwardly relative to a outer surface 57 of said body 50. On the outward facing surface 29 of the rejuvenation 55 a reagent 30 is provided on each finger 53. The reagent can be the same on each finger but on different fingers 53 different reagents 30, 30A, 30B . . . can be provided, for example, in order to perform different, whether or not related tests. The cylindrical body 50 has an outer diameter D3, which is roughly equal to the inner diameter D2 of the body 13, so that it can be inserted from the top 15 into the body 13, preferably with fingers 53 in the direction of the end 14. The outer surface 57 can then adjoin against the inside of the body 13, while the surface 29 is kept at a distance thereof. This allows the reagent 30, 30A, 30B . . . to come into proper contact with plasma collected in the space 27. Of course, the reagent can be provided or applied otherwise, for example, directly onto the surface 57, if this is kept remote from the wall of the body 13, or on an inward-facing surface of the insertion element 32, in which case it is beneficial when at least fingers 53 at least at the position of the reagent 30 are at least partially transparent.

Figure 4:
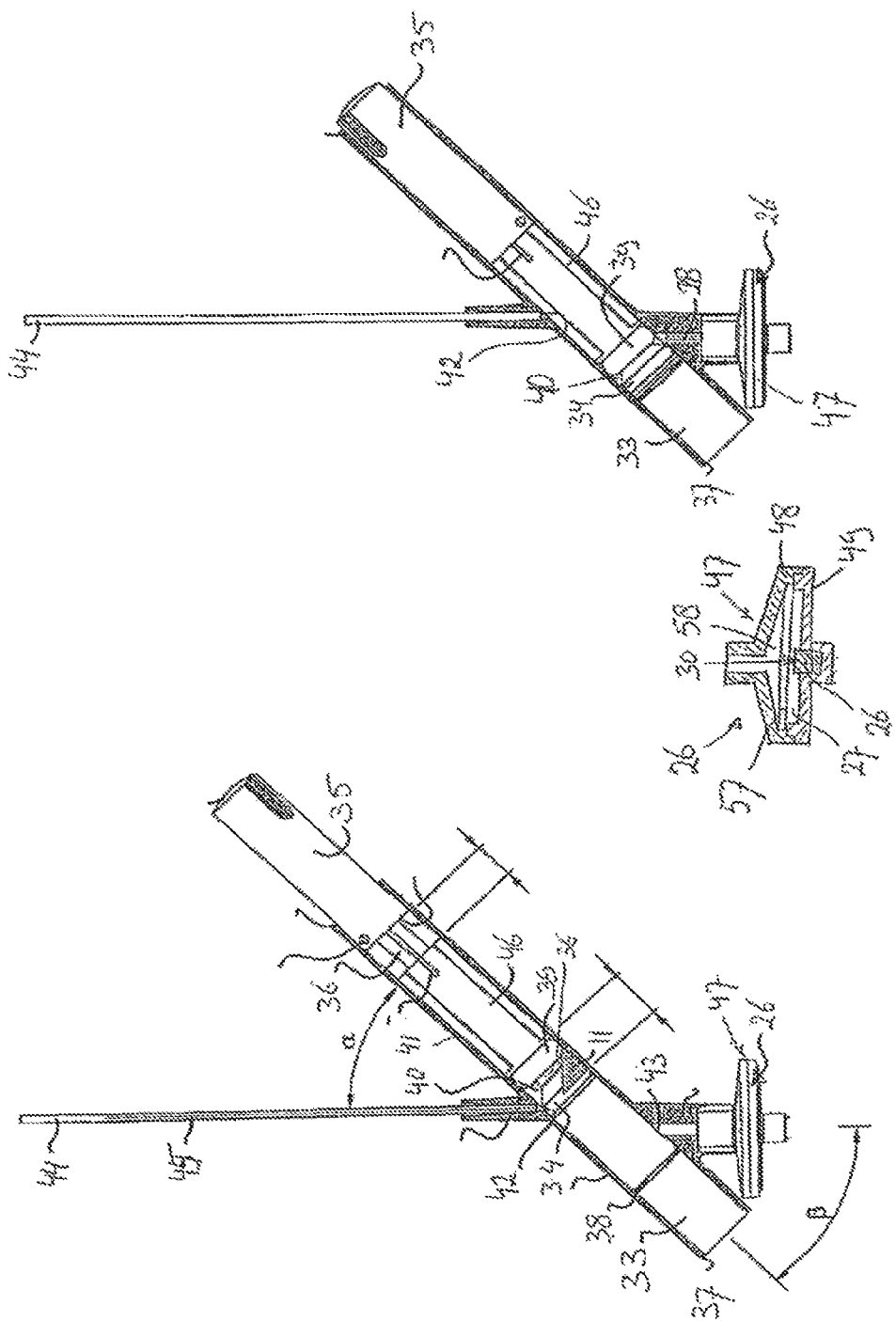
FIGS. 4A and B show in partial cross sectional side view of an alternative embodiment of a device of the invention, respectively in an initial and a final position.
FIG. 4C show schematically in cross sectional side view a filter for a device of FIG. 4.

FIGS. 4A and B show schematically a device 1 according to the invention, in an alternative embodiment, of which the base is described in NL 1016646, which publication is incorporated by reference in its entirety herein, at least as regards the operation for separating plasma from blood.

This device 1 includes a hollow cylindrical body 33 wherein a first piston 34 is sealingly movable with the help of a pressure body 35 between a first position wherein the pressure body rests against an end of first stem 36 which is connected to the first piston and a second position, such as rotated relative to the first position over an angle of about 90 degrees around an axis through the body 33, along the stem 36. In the first position the first piston 34 can thus be pushed in the direction of a lower end 37 of the body 33 using the pressure body 35, up against an abutment 38. A second piston 39 with stem 46 is provided around stem 36, and seals off both the stem as well as the inside of the body 33. The second piston 39 is for instance a rubber ring. Between the first and second piston 34, 39, a treatment chamber 40 is enclosed, whose volume is variable. It can contain a treatment liquid or other material, such as a buffer 11, for example, a phosphate buffer, similar to FIG. 1-3. In a wall 44 of the body 33 an inlet 42 and a outlet 43 have been fitted. A capillary 44 can be placed in the inlet, so that the contents of the capillary 44 can be sucked into the body between the two pistons 34, 39, in the treatment chamber 40, as will be described. To the outlet 43 a filter 26 is fitted, wherein and/or through which at least the contents of the treatment chamber 40 may be forced.

In a starting position, shown in FIG. 4A, the pistons 34, 39 are positioned relatively high in the body 33 and relatively close to each other. The inlet opens preferably precisely in the treatment chamber, which treatment chamber 40 has a relatively small volume. A capillary 44 filled with whole blood 45 as a sample is placed in the inlet 42. By pressing the first piston 34 in the direction of the lower end 37 of the body it passes the outlet 43 while the volume of the treatment chamber 40 is increased, because the second piston 39 will not, or at least not completely, follow the movement of the first piston 34 in a first portion of the maximum stroke, that is, the maximum distance over which the pressure body 35 can move from the starting position in the direction of the lower end 37 before it is brought in the second position. Due to the increase in the volume of the treatment chamber 40 the content of the capillary will be sucked into the treatment chamber and mixing it with the treatment liquid 11.

The pressure body is then brought into the second position relative to stem 36, so that it can be pressed further in the direction of the lower end 37 over the stem 36, whereby the second piston 39 is pressed in the direction of the first piston 34. The volume of the treatment chamber is thereby reduced back, in particular minimized and the mixture of the treatment liquid and the sample is pushed through outlet 43, into and/or through the filter 26. The filter can be any suitable filter, for example, a glass fiber filter. The blood is thereby separated from the plasma, because the plasma is pressed through the filter, stripped of blood particles such as erythrocytes and leukocytes.

According to the invention in and/or at the filter 26 at least one test surface 29 is provided as shown in FIG. 4C, formed by or comprising a reagent 30, such as for instance described above. Because the plasma is forced through the filter, this comes into direct and intensive contact with any test surface 29 and consequently with any of the reagent 30, allowing an almost instantaneous readout of the test result. The advantage is that it need not be supplied to an external reagent surface, whereby contamination of the plasma and/or the reagent can be prevented.

Moreover, the plasma can be collected in the filter 26, or at least in the housing 47 thereof, whereby pollution and in particular contamination of the environment can be prevented. This is of particular importance in case of use in biological samples such as blood in which disease causing agents may be present.

In FIG. 4C a schematic filter 26 for a device according to FIG. 1. 4A and B is show, which filter 26 includes a housing 47. The housing 47 is at least partially, and preferably completely transparent, so that the filter surface 48 or at least a part thereof to which reagent 30 is supplied can be seen without the need to open housing 47. This prevents pollution of plasma, reagent and/or the environment. The housing 47 may, for example, include two housing parts 48, 49, attached to each other while including a filter element 57 as previously described, for separation of blood plasma and blood cells. In the first housing part 48 above the filter element 57, a chamber 58 is provided at a side which faces outlet 43 during use, where blood cells remain. In the second housing part 49 a collection chamber or space 27 is provided in which the separated plasma 28 is collected. In this space, at least a surface 29 is provided on or in which reagent is included for reaction with the blood plasma. This surface 29 may for instance be provided on the filter element 57, at the side facing collection chamber 27, whereby the surface may for instance be provided in porous form so that intensive contact is made between plasma and reagents. As shown in FIG. 4C, the surface 29 can also be provided on the inside of the housing 47, in the collection chamber 27, or both. In this embodiment the second housing part is transparent at least at the position of the surface 29, which here is provided on a block 59, so that, for example, discoloration of the block as a result of the reaction between elements of, or in the plasma and the reagent 30 is visible from outside the housing 47.

The invention is by no means confined to embodiments provided in the drawings and description. Many varieties are possible within the scope outlined by the claims of the invention.

For example, when using a filter, a housing can be used in which the plasma is at least partially collected, wherein the housing is at least partially transparent, and the reagent is provided therein. This offers the advantage of good protection against pollution and/or contamination. Moreover, the device or at least the plasma collected therein can then be used for further tests. The device in its entirety or the filter and/or housing can, for example, be sent to a laboratory, where further tests can be conducted, for example, in order to verify or further investigate a first indication obtained with the reagent.

Detection of Analytes in Blood Using the Device

A device of the present invention can be provided with a reagent for detection, ie for the determination of the quantitative, semi-quantitative or qualitative presence of an analyte such as a chemical or biological substance or microorganisms in the blood plasma.

For instance, a reagent can be used which may indicate the presence of *Helicobacter pylori*, or that indicates an excess or deficiency of coagulation factors.

Also reagents can be used that indicate the presence of antigens such as an extent in which they must be present or that a limit is exceeded, for example antigens by which the presence of tumors can be demonstrated or can be made credible.

Reagents can also be applied with which the presence of, for example, vitamins can be determined.

Reagents can further be used with which by an overshooting or undercutting of a threshold or limit it can be indicated whether the overshoot is detrimental to the patient. Such reagents can advantageous be combined with a reagent that indicates overshooting or undercutting of that limit. Furthermore reagents can be applied with which a therapeutic blood level of a substance can be determined, for example a drug or toxin, such as a drug which, for optimal functioning, depends on an optimal blood level that may not be exceeded because of, for instance, undesirable side effects. Also combinations of reagents as mentioned can be applied. These reagents and applications are of course only illustrative, and should not be interpreted restrictively.

In the present description, the term "reagent" or "reagents" or similar wording should at least be understood to include antibodies or enzymes, which means that tests can be applied that are antibody or enzyme-based.

Several reagents and other markers can be applied, such as antigens, chemical reagents, enzymes, chemical markers and the like. Reagents and markers could be used to indicate problems with heart, liver, kidney or other organs, glucose abnormalities such as diabetes, cholesterol disorders, defects in one or more hormones or cytokines, diagnostic parameters in general and such, viral or bacterial abnormalities such as influenza, malaria, hepatitis, HIV, inflammation, MS, ME, and other indicators, especially for existing and/or potential health problems. Deviations in this context should be understood as such deviations from normal values of which it can be expected that, for the patient at issue, these values indicate or should indicate to a physician that further investigation or intervention is needed by, for example, administration of drugs, fluids, or nutrients or by surgical intervention.

Examples of reagents, which are by no means limiting the invention, include for example antibodies for HTLV I and/or II, cystatin C or markers for kidney functions such as cardiac or cardiovascular problems, heart attacks (myocardial infarction) and/or stroke, monoclonal antibodies, coagulation reagents such as lupus anticoagulant sensitive or insensitive reagents, PSA antigen, HBS-1, HLA antibodies, HbA(1c) or GlyHb in hemoglobin measurement.

In a first example of an embodiment of a surface 29, a cholesterol reagent, CHOD-Pap (Boehringer-Mannheim GmbH) as a reagent 30, which is suitable for the demonstration of cholesterol (total cholesterol, HDL or LDL) was applied on the inside of the tubular section 13. In the chamber 10 a quantity of diluent (buffer) was provided (e.g. 220 microliters), after which blood was diluted therein (eg. 60 microliters of blood, effectively diluting the blood 4 to 5 times). By depression of the second part in the first part, as described above, 220 microliter of plasma was collected in the first space 27. This plasma was brought into contact with the reagent by shaking (horizontal rocking), as a result of which the reagent discolored from a neutral color to a distinctive color, in this case red, clearly visible from the outside. By this, it was found that the cholesterol level in the blood was higher than a threshold of 6.5 mmole/l. Control measurements of whole blood drawn by venous collection and tested in a laboratory and drawn by means of a finger prick and tested in a laboratory showed that the blood indeed had a value above that threshold.

An embodiment of special preference for the detection of markers for kidney function, liver, heart attack and/or stroke will be described below.

This embodiment of special preferences can in particular be applied to the quantitative, semi-quantitative or qualitative detection of FABP in samples of body tissue or body fluids. Fatty acid-binding protein (FABP) is a protein known as an early marker for damage to specific tissues wherein each tissue type is characterized by its own FABP type. FABP are 15 kDa cytosolic proteins involved in intracellular binding of fatty acids and are expressed in nine different isoforms, each named after the tissue in which it was first described.

Heart-FABP (H-FABP or heart-type)
Liver-FABP (L FABP or liver-type);
Intestinal-FABP (I-FABP or small intestine type),
Ileal-FABP (ILBP or ileum-type)
Brain-FABP (B-FABP or brain-type)
Adipocyte-FABP (A-FABP or fat cell-type)
Epithelial/epidermal-FABP (E-FABP or epithelial cell-type),
Testicular-FABP (H-FABP or testicular-type) and
Myelin-FABP (M-FABP or nerve cell-type).

To date, there are no rapid tests for FABP that can give results in less than a few minutes. The rapid determination of FABP may lead to a rapid diagnosis of tissue damage and early commencement with the proper therapy in particular in life threatening conditions such as heart disease or stroke. Measurements on the quantity of specific FABPs may, amongst others, but not exclusively, be applied for the diagnosis of myocardial injury (H-FABP), skeletal muscle injury (H-FABP), liver damage (L-FABP), kidney damage (L-FABP and/or H-FABP), intestinal damage (including I-FABP, ILBP and/or L-FABP), brain damage (B-FABP and/ or H-FABP), and in the diagnosis of a series of disorders to the lipid metabolism, diabetes, inflammatory disorders, multiple sclerosis, atherosclerosis, cancer and tissue rejection after transplantation.

The present invention provides for the detection of basically any of the above FABPs in each isoform in which it can occur in an animal or human patient, wherein the detection, in connection with the desired specificity, is preferably performed on the basis of an immunoassay, and preferably in blood.

Immunoassays for the detection of FABP are in principle known to the skilled person, and such assays are suitable for use in the present invention. An example of an available immunoassay takes the form of a sandwich ELISA (Pelser M M A L. 2004. "Fatty acid-binding protein as plasma marker for tissue injury." Thesis University of Maastricht, Netherlands ISBN 90-9018161-X, Chapter 3, p. 43-51; Wodzig K W H, Pelser M M A L, van der Vusse G J, Roos W, Glatz J F C. One-step enzyme-linked immunosorbent assay (ELISA) for plasma fatty acid-binding protein. Ann Clin Biochem 1997; 34:263-8). This assay, with a total duration of 45 minutes, is the fastest, most specific and sensitive H-FABP ELISA which is commercially available. This assay makes use of two different monoclonal antibodies, each directed to a different epitope of H-FABP. One of these monoclonal antibodies act as capture-antibody and is attached to a detection surface. The other antibody is conjugated with horseradish peroxidase (HRP) and serves as detection-antibody. The monoclonal antibodies which are applied in this assay are described in more detail elsewhere (vide Pelser M M A L. 2004. supra Chapter 3, p. 43-51 and Chapter 4, p. 53-67; Roos W, Eymann E, M Symannek, Duppenthaler J, Wodzig K W H, Pelser M M A L, Glatz J F C. "Monoclonal antibodies to human heart fatty acid-binding protein." J Immunol Methods 1995; 183:149-53). The detection may, after formation of a capture-antibody/H-FABP/detection-antibody complex, be detected by using a HRP-specific enzyme substrate, such as the chromogen tetramethyl benzidine (TMB) which after conversion by HRP provides a blue reaction product which can be detected spectrophotometrically by measuring the absorption at 450 nm.

The skilled person will understand that many variations on the above detection principal can be used in aspects of the present invention.

Thus, antibodies against other FABP types then H-FABP can be used to detect other isoforms of this protein. Also other epitopes can be applied for the binding between the antibody and FABP. The development of antibodies against other epitopes of a particular FABP for which an antibody to an epitope is already available, or the development of antibodies that exhibit specific binding with other FABP isoforms is within the reach of the skilled person and need not be described in detail here.

An antibody that can be applied as a reagent in aspects of the present invention can be a polyclonal or a monoclonal antibody. Preferably monoclonal antibodies are used. Antibodies can include complete immunoglobulins or a fragment thereof, wherein immunoglobulins can be selected from the different classes and isotype, such as IgA, IgD, IgE, lgG1, IgG2a, lgG2b and lgG3, IgM, etc. Fragments thereof may comprise Fab, Fv and F(ab')2, Fab', and the like. Furthermore, aggregates, polymers, and conjugates of immunoglobulins or fragments thereof can suitability be applied as long as the binding affinity for a given FABP is maintained.

The element which is commonly referred to herein as reagent 30 will usually be formed by the capture-antibody. This capture-antibody can be affixed to the surface of any element of the device 1 that limits space 27 (or first collection means 27) and which surface is faced inwardly towards space 27 so that the capture-antibody is or can be in direct contact with blood plasma 28. The capture-antibody can thus be applied to (at least part of) stem 18, (at least part of) tubular element 13, or at least a surface 29 as described herein. Also, as described in the examples below, the capture-antibody can be affixed to a porous element which is affixed on or in a surface of any element of the device 1 that limits space 27 (or first collection means 27) and which surface is faced inwardly towards space 27 so that an improved contact between the capture-antibody and the plasma can take place. Adherence of the capture-antibody to a solid surface, for example, can be achieved through a biotin-(strept)avidin link. The capture-antibody can optionally be provided with a paramagnetic label so that it can be collected from a liquid and immobilized to a solid phase at any time during the reaction by magnetic attraction.

The stem (18) is preferably a form that allows insertion into a tubular element of the pressure means. The stem can tubular, meaning that the interior is hollow, the stem can be solid, and in cross section may be round, elliptical, squared, triangular or oblong. The stem may include elements onto which reagents are or can be applied. Such elements can be porous or solid. Preferably the reagent-bearing elements by their porous nature support the uptake of diluted plasma from the collection means. Preferably, the reagent-bearing elements are capable of taking up more than 10%, preferably more than 20, 30, 40 or 50% of the separated plasma from the collection means 27. As a result, the diffusion distance between the capture-antibody and the FABP present in the liquid phase, wherein said FABP is preferably present in a form wherein it is complexed with a detection-antibody, is substantially shortened. It is highly preferred that the reagent-bearing element supports a capillary flow, whereby the plasma is drawn into the porous reagent-bearing element under the influence of capillary force as a result of which it is brought into contact with immobilized reagent (i.e. immobilized capture-antibody).

Preferably, the test of the present invention is in the form of a sandwich ELISA, wherein further a detection-antibody is used for the detection of the binding of the FABP to the capture-antibody. The binding of the detection-antibody to FABP may in principle occur prior to, during or after the binding of FABP to the capture-antibody. Preferably, it is first allowed that the detection-antibody binds to an FABP present in the body sample and then this complex is allowed to bind to the immobilized or to-be immobilized capture-antibody. In order to achieve this, the detection-antibody can be very suitably added to the diluent 11 in chamber 10 of the device of the invention. In an alternative embodiment, the antibody can be added to a (porous) element with which a known quantity of blood is introduced into the diluent 11. Such an element may take the form of a sponge, wherein the detection-antibody is present so that it can mix directly with the sampled blood, before the whole sponge is introduced in the diluent 11 in order to transfer blood and detection-antibody from sponge to diluent 11.

In another alternative embodiment, the antibody can be added to space 27 after the plasma is collected therein, or may be already present in space 27 before the blood plasma is collected therein. It is important that the detection-antibody is mixed homogeneously with the blood or blood plasma under conditions in which binding to FABP occurs or is possible. In an embodiment wherein a capture-antibody is applied that is to be immobilized and which is first allowed to react with FABP in the liquid phase, this capture-antibody can also be added to the diluent 11, to a blood drawing element or blood collection element or to plasma after separation of plasma in space 27. In fact, every possible combination or sequence is possible, as long as the end result provides an immobilized complex of capture-antibody-/-FABP-/-detection-antibody.

The detection-antibody may be labeled with any appropriate detection label, such as colloidal gold or silver, streptavidin, biotin, microspheres, latex beads, peroxidase, streptavidin-labeled horse radish peroxidase (HRP), phosphatase, alkaline phosphatase (AP) chromogenic labels, fluorescent labels, phosphorescent labels, chemiluminescent labels, secondary antibodies or any other suitable label with which detection of successful binding can be established. An optional secondary antibody may comprise any of the above labels.

Preferably, colloidal gold is used, because no washing steps are needed and a simple one-step test is obtained. Colloidal gold consists of discrete red particles with a diameter of 10 nm to 100 nm and a very high extinction coefficient. When concentrated at a solid surface colloidal gold can very easily be observed visually as a red color. Preferably, the capture-antibody is therefore applied in a recognizable pattern to the surface of any element of the device 1 that limits space 27 and which surface is faced inwardly towards space 27 so that the capture-antibody is in direct contact with blood plasma 28 and which surface can be observed at least in part from the outside of the device.

The skilled person will understand that lateral flow applications are envisioned in the present invention. The skilled person will also understand that alongside and parallel to the primary test a secondary test can be performed with which either a second FABP is detected, or by which a control-reaction is provided.

Body samples which can be used in a test in accordance with the invention are in principle not limited to blood. Also other body samples such as tissue samples, or a sample of urine, feces, saliva, tear fluid, mucus, sputum, semen, cervical secretions, cerebrospinal fluid, vomit, nasal secretions, sweat, amnion fluid, or breast milk can be tested.

In a further aspect, the present invention provides a kit of parts, the components of which are preferably packed together. The kit according to the invention preferably includes:

- tube with diluent (first part 2 of device 1, according to the invention as shown in FIG. 1, comprising a chamber 10 with a diluent 11 as described above, and preferably with outer screw thread 7 as shown in the figures);
- Optionally a sponge (not shown in the Figure) which provides for the possibility of sampling a known quantity of blood for introduction into the diluent 11 in chamber 10 of the device 1. This element can be applied to introduce a known quantity of a blood sample into the diluent in the chamber of the device (typically about 60 µL of blood, but this amount may vary), whereby the blood constituents are diluted in the diluent;
- A blood filter (piston part 12 comprising an at least partially transparent tubular element 13 with an open lower end 14 wherein a filter 26 is provided through which at least plasma can pass but through which red blood cells can not pass, and which piston part can be introduced into chamber 10 and can sealingly slide along the wall of chamber 10 towards bottom 4);
- A cap (flange part 19 with a stem 18 as shown in FIG. 1 whereby on the lower end 24 of the stem 18 a stop 25 is provided which can seal the open-ended tubular element 13 above filter 26 as shown in FIG. 3, so that the return of blood plasma 28 from the first collection means 27 is prevented, and where the flange part 19 on the top and connects to an apron 21 that extends outwardly and is fitted with inner screw thread 22 that can fit onto the outer screw thread 7 of the first Part 2 of device 1, according to the invention as shown in FIG. 1);
- A capture-antibody that can bind specifically to a first epitope of FABP (reagent 30). The capture-antibody may advantageously be in a form in which it is immobilized, in or on a surface of a space 27-facing side of an element that limits space 27 and that can be observed from the outside of the device. An antibody suitable for use as capture-antibody for the detection of H-FABP is anti-human monoclonal antibody H-FABP 67D3 (such as available from Hycult Biotechnology BV, Uden, Netherlands). A suitable surface is a porous part having capillary action, which can for example be applied in lateral flow detection;
- Optionally a detection-antibody that can bind specifically with a second epitope of FABP, which is different from the first epitope and wherein both antibodies do not materially affect each others binding to FABP in a detrimental manner. The detection-antibody may advantageously be provided in the diluent. An appropriate concentration of a detection in the diluent is 5 to 20 µg/L. An antibody suitable for use as detection-antibody for the detection of H-FABP is anti-human monoclonal antibody H-FABP 66E2, (such as available from Hycult Biotechnology BV, Uden, Netherlands).

The application of the device and the detection system in accordance with the invention provides a point-of-care (POC) rapid test, ie a rapid test for use by general practitioners, in an ambulance, in a hospital or as a home-test for detection of FABP in plasma.

A method of detecting FABP in a sample of blood from a patient preferably includes the following steps:

- providing a device of the present invention as described above;
- introducing a known quantity of blood in said diluent in said chamber, whereby optionally a porous body is applied wherein a fixed amount of blood can absorb in order to provide a pre-determined amount of blood in the diluent, and mixing the blood with the diluent;
- separating red blood cells from blood plasma by engaging the separation means of the device;
- contacting FABP in said blood or blood plasma with at least one of said detection-antibody and capture-antibody under conditions wherein specific binding occurs between the antibody and the FABP, and
- detecting the specific binding.

The different variations in embodiments on this process are explained in detail above.

The present invention will now be illustrated by the following examples which are in no way limiting the invention.

EXAMPLE

Developing a point-of-care (POC) Rapid Test

A Test for Use in General Practitioners Office, Ambulance, Hospital or as Home Test for Detection of FABP in Plasma The test provides for the immunochemical determination of the presence of an increased concentration (>6 µg/L) of heart-type fatty acid-binding protein (H-FABP) in plasma, and is combined with a device as described herein. The time between the taking of the blood sample and obtaining the test result is less than 90 seconds.

The present embodiment describes in detail a kit-of-parts as described above and as envisioned by the inventors. This embodiment includes:

A lancet (finger pricker) to a cut in a fingertip in order for provide a blood sample;

A tube (chamber) comprising a diluent (100 mM HEPES EDTA (pH 7.4) and 0.9% NaCl);

A sponge for collecting a defined amount of blood;

A blood filter for the separation of plasma and blood cells at the tip of a tubular element;

A cap fitted with a stem with stop with which, respectively, the top side of the chamber (cap) and the return through the blood filter (stop) can be sealed.

The diluent is provided with mouse monoclonal antibody 66E2 (available at Hycult Biotechnology BV, Uden, Netherlands) directed against human heart-type FABP (this monoclonal is referred to as the 'first antibody', $mAb_{detect}$) and is conjugated to colloidal gold or another appropriate color indicator. An appropriate concentration of $mAb_{detect}$ in the diluent is 5 to 20 µg/L.

The sponge is applied to introduce approximately 60 µL of blood from a blood sample into the diluent in the chamber of the device, in which the blood is diluted. FABP present in the blood sample will essentially instantaneously bind to the gold-conjugated monoclonal antibody $mAb_{detect}$ present in the diluent to form a FABP-$mAb_{detect}$-gold complex. The shaking of the contents of the chamber for 40 seconds on average, for example, contributes to dissolving the blood in the diluent and the complete binding of FABP by $mAb_{detect}$.

Hereafter the blood filter is placed in the chamber and is pressed slowly downwards in the direction of the bottom of the chamber. The blood filter is pressed with force against the diluted blood containing the blood-FABP $mAb_{detect}$-gold complex, so that blood plasma together with the FABP-$mAb_{detect}$-gold complex is pressed upwards through the blood filter while the red blood cells are arrested and remain in the chamber. The blood plasma together with the FABP-$mAb_{detect}$-gold complex is collected at the other side of the blood filter in the inner space of the tubular element. After placing in the tubular element the sealing cap equipped with stem with stop the open end of the tubular element above the blood filter is sealed, preventing the return through the blood filter. At the same time, the chamber is sealed at the top by the cap.

In the present embodiment the stem which connects the stop to the cap is provided in the form of a hollow tube having a wall which is at least partially transparent or open over a length of about 10 mm. The transparent or open part of the wall of the stem begins preferably at about 2-3 mm from the lower end of the stem and extends preferably to about 12-13 mm from the lower end of the stem. The hollow tube of the stem is filled with a porous part having capillary activity to a liquid, and which porous part is visible from the outside of the device by virtue of the at least partially transparent or open wall of the stem. At a distance of about 5 mm from the lower end of the stem the porous part comprises immobilized thereto a quantity ca. 200 ng of monoclonal antibody 67D3 (Hycult Biotechnology BV, Uden, Netherlands), directed against human heart-FABP type (which is referred to as the 'second antibody', $mAb_{capture}$) and which antibody recognizes an epitope on human heart-type FABP that is different from that recognized by $mAb_{detect}$.

Similarly, the porous part at a distance of about 10 mm from the lower end of the stem comprises immobilized thereto a monoclonal antibody directed against another protein (for example, a control or reference or second test protein). The total length and volume (i.e. the size) of the porous part is preferably such that a significant portion (about 100 µL) of the diluted plasma sample is absorbed in the porous part.

After absorption of the plasma into the porous part the FABP-$mAb_{detect}$-gold complex will bind to the second monoclonal antibody $mAb_{capture}$ immobilized thereon under the formation of a colored band that is visible through the transparent or open wall of the stem. The intensity of this colored band will increase with the concentration of FABP in the blood sample. In the event the FABP concentration in the original blood sample is <6 µg/L, no colored band will be visible.

Similarly, another protein that is present in the blood will bind to the specific antibody that is immobilized on the porous section at a distance of 10 mm from the lower end of the stem as described above, and if the diluent is also provided with an a gold-conjugated antibody against another epitope of that protein, this complex will be visible as a colored band on the porous part at a distance of 10 mm from the lower end of the stem. This reaction can be used as a control on the presence of blood plasma in the test and thus a proper implementation.

The invention claimed is:

1. A device for detecting fatty acid binding protein (FABP) in a blood sample from a patient, the device comprising the following elements:

a) separator for separating blood into blood plasma and red blood cells, wherein said separator comprises:

a chamber for receiving a blood sample and comprising a diluent for said blood sample;

a filter through which blood plasma from a diluted blood sample and said FABP, optionally complexed to an antibody, can pass but at least red blood cells cannot, and a pressurizor that presses through said filter at least part of the blood sample to provide separated blood plasma, and b) a collector for the separated blood plasma, wherein said separator and/or said collector and/or said diluent is provided with a detection-antibody against a first epitope of FABP, said detection-antibody being conjugated with a detectable label and contacts blood plasma, and said collector is provided with a capture-antibody against a second epitope of FABP which is different from said first epitope, wherein said capture-antibody is provided in said collector in immobilized form and contacts said separated blood plasma, and wherein said filter is provided at or near the end of a tubular element which can be inserted in said chamber, and wherein said collector is formed by the interior part of said tubular element.

2. Device according to claim 1, wherein said capture-antibody is immobilized on or in an insertion element that can be inserted into said collector.

3. Device according to claim 1, wherein said detection antibody is provided in said diluent.

4. Device according to claim 1, wherein said FABP is selected from the group consisting of H-FABP, L FABP, I-FABP, ILBP, B-FABP, A-FABP, E-FABP, T-FABP and M-FABP.

5. Device according to claim 1, wherein said detectable label is selected from the group consisting of colloidal gold, colloidal silver, streptavidin, biotin, microspheres, latex beads, peroxidase, streptavidin-labeled horse radish peroxidase (HRP), phosphatase, alkaline phosphatase (AP), Chromogenic labels, fluorescent labels, phosphorescent labels, chemiluminescent labels and secondary antibodies.

6. Device according to claim 1, wherein the collector is at least partially transparent, such that the attachment site of said immobilized capture-antibody is at least partially visible from the outside of the device.

7. Method for the detection of FABP in a blood sample from a patient comprising the following steps:
introducing a predetermined amount of blood into the chamber of the device of claim 1, optionally by using a porous body wherein a predetermined amount of blood can be absorbed which is then provided to said diluent in said chamber, and mixing the blood with the diluent;
separating red blood cells from blood plasma by filtration by engaging the separator of the device;
contacting FABP in said blood or blood plasma with said detection-antibody under conditions wherein specific binding occurs between the antibody and the FABP, and detecting the specific binding.

8. Method according to claim 7, wherein said detection-antibody is provided in said diluent.

9. Method according to claim 8, wherein a detection-antibody-FABP complex is formed which binds to the immobilized capture-antibody.

10. Method according to claim 7, wherein said FABP is selected from the group consisting of H-FABP, L FABP, I-FABP, ILBP, B-FABP, A-FABP, E-FABP, T-FABP and M-FABP.

11. Kit-of-parts, comprising the device of claim 1 and at least one specific antibody that reacts with FABP suitable for being introduced into the collector of said device.

12. Kit-of-parts, according to claim 11 further including an element for taking up and releasing a predetermined amount of blood.

\* \* \* \* \*